United States Patent
Inoue et al.

(10) Patent No.: US 8,188,024 B2
(45) Date of Patent: May 29, 2012

(54) SURFACTANT COMPOSITION

(75) Inventors: Masaki Inoue, Wakayama (JP);
Yasuhiro Doi, Wakayama (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 13/128,195

(22) PCT Filed: Dec. 24, 2009

(86) PCT No.: PCT/JP2009/007153
§ 371 (c)(1),
(2), (4) Date: May 6, 2011

(87) PCT Pub. No.: WO2010/073644
PCT Pub. Date: Jul. 1, 2010

(65) Prior Publication Data
US 2011/0212880 A1    Sep. 1, 2011

(30) Foreign Application Priority Data
Dec. 24, 2008   (JP) .................. 2008-327293

(51) Int. Cl.
*C11D 1/29* (2006.01)
*C11D 1/72* (2006.01)
*C11D 1/83* (2006.01)

(52) U.S. Cl. ........ 510/128; 510/131; 510/136; 510/137; 510/138; 510/158; 510/159; 510/235; 510/238; 510/424; 510/427; 510/432; 510/435; 510/505; 510/506

(58) Field of Classification Search .................. 510/128, 510/131, 136, 137, 138, 158, 159, 235, 238, 510/424, 427, 432, 435, 505, 506
See application file for complete search history.

(56) References Cited

U.S. PATENT DOCUMENTS

| 4,395,364 A | 7/1983 | Murata et al. |
| 2006/0105933 A1 | 5/2006 | Hayashi et al. |
| 2009/0253603 A1 | 10/2009 | Uchiyama et al. |

FOREIGN PATENT DOCUMENTS

| EP | 1 696 023 A1 | 8/2006 |
| JP | 55-84399 A | 6/1980 |
| JP | 56-72092 A | 6/1981 |
| JP | 2004/352943 A | 12/2004 |
| JP | 2006-36952 A | 2/2006 |
| JP | 2006-265547 A | 10/2006 |
| JP | 2007-55997 A | 3/2007 |
| JP | 2009-155611 A | 7/2009 |
| JP | 2009-185252 A | 8/2009 |
| WO | WO 2008/004342 A1 | 10/2008 |

OTHER PUBLICATIONS

International Search Report, dated Mar. 30, 2010 in PCT/JP2009/007153.
International Preliminary Report on Patentability and Written Opinion of The International Searching Authority dated Aug. 18, 2011, for Application No. PCT/JP2009/007153.

*Primary Examiner* — Gregory Delcotto
(74) *Attorney, Agent, or Firm* — Birch, Stewart, Kolasch & Birch, LLP

(57) ABSTRACT

According to the present invention, provided is a surfactant composition having excellent fluidity after long-term storage at a low temperature (5 degrees Celsius) and excellent foamability when diluted. It is considered that the reason why the composition of the present invention has excellent fluidity after long-term storage at a low temperature (5 degrees Celsius) and excellent foamability when diluted is because the sulfate surfactant has a predetermined amount of oxypropylene groups, thereby suppressing crystallization.

6 Claims, No Drawings

SURFACTANT COMPOSITION

FIELD OF THE INVENTION

The present invention relates to a surfactant composition which has good fluidity over a wide temperature range even if it contains a specific sulfate surfactant at a high concentration and which serves as a detergent having excellent foamability when diluted.

BACKGROUND OF THE INVENTION

Polyoxyethylene alkyl ether sulfate or alkyl ether sulfate, which is generally used as a sulfate surfactant, has extremely poor fluidity at a high concentration and is difficult to handle.

In order to solve this problem, Patent Document 1 proposes a surfactant composition formed by combining (a) polyoxyethylene alkyl ether sulfate or alkyl ether sulfate with (b) one or more of glyceryl ether or diglyceryl ether having an alkyl or alkenyl group having 4 to 24 carbon atoms and (c) a water-soluble salt, in which the content of the component (a) is not less than 40 wt. %.

Furthermore, Patent Document 2 proposes a surfactant composition formed by combining (a) a polyoxyethylene alkyl ether sulfate or alkyl sulfate with (b') an alkylene oxide adduct of alcohol, represented by: $R^2O-(AO)_m-R^3$, and (c) a water-soluble salt, in which the content of the component (a) is not less than 40 wt. %.

However, these surfactant compositions are not sufficiently satisfactory in terms of the fluidity after long-term storage at a low temperature (5° C.) and the foamability when diluted.

PRIOR ART DOCUMENT

Patent Document
[Patent Document 1] JP-A-2006-265547
[Patent Document 2] JP-A-2007-55997

SUMMARY OF THE INVENTION

The present invention provides a surfactant composition containing the following components (A), (B) and (C), wherein the content of the component (A) is 40 to 75 wt. %, (A) a sulfate surfactant represented by the following general formula (1):

$$R^1O-(PO)_m(EO)_nSO_3M \qquad (1)$$

wherein $R^1$ represents a saturated or unsaturated hydrocarbon group having 8 to 18 carbon atoms; PO represents a propyleneoxy group; EO represents an ethyleneoxy group; m and n represent an average mole number of added PO and EO, respectively, are the same as or different from each other, and independently represent a number within the ranges of $0 \leq m < 1$ and $0 \leq n < 5$; and M represents a cation;

(B) one or more of compound(s) selected from the group consisting of the following (B-1) and (B-2):

(B-1) an alkylene oxide adduct of alcohol represented by the following general formula (2):

$$R^2O-(AO)_t-R^3 \qquad (2)$$

wherein $R^2$ represents a linear or branched alkyl or alkenyl group having 8 to 10 carbon atoms; AO represents an alkyleneoxy group having 2 to 4 carbon atoms; t represents an average mole number of added AO and represents a number of 0.5 to 4.0; and $R^3$ represents a hydrogen atom or a methyl group;

(B-2) a monoalkyl (having 6 to 18 carbon atoms) or monoalkenyl (having 6 to 18 carbon atoms) glyceryl ether; and (C) a water-soluble salt.

DETAILED DESCRIPTION OF THE INVENTION

The present invention is to provide a surfactant composition having excellent fluidity after long-term storage at a low temperature (5° C.) and excellent foamability when diluted.

The present inventors have found that a composition having excellent fluidity after long-term storage at a low temperature (5° C.) and excellent foamability when diluted can be obtained by using a specific sulfate surfactant represented by the above-mentioned general formula (1) in combination with an alkylene oxide adduct of alcohol and a water-soluble salt.

According to the present invention, provided is a surfactant composition having excellent fluidity after long-term storage at a low temperature (5° C.) and excellent foamability when diluted. It is considered that the reason why the composition of the present invention has excellent fluidity after long-term storage at a low temperature (5° C.) and excellent foamability when diluted is because the sulfate surfactant has a predetermined amount of oxypropylene groups, thereby suppressing crystallization.

Hereinafter, the present invention is described in more detail.

The present invention is a surfactant composition containing the following components (A), (B) and (C), wherein the content of the component (A) is 40 to 75 wt. %, (A) a sulfate surfactant represented by the following general formula (1):

$$R^1O-(PO)_m(EO)_nSO_3M \qquad (1)$$

wherein $R^1$ represents a saturated or unsaturated hydrocarbon group having 8 to 18 carbon atoms; PO represents a propyleneoxy group; EO represents an ethyleneoxy group; m and n represent an average mole number of added PO and EO, respectively, are the same as or different from each other, and independently represent a number within the ranges of $0 \leq m < 1$ and $0 \leq n < 5$; and M represents a cation;

(B) one or more of compound(s) selected from the group consisting of the following (B-1) and (B-2):

(B-1) an alkylene oxide adduct of alcohol represented by the following general formula (2):

$$R^2O-(AO)_t-R^3 \qquad (2)$$

wherein $R^2$ represents a linear or branched alkyl or alkenyl group having 8 to 10 carbon atoms; AO represents an alkyleneoxy group having 2 to 4 carbon atoms; t represents an average mole number of added AO and represents a number of 0.5 to 4.0; and $R^3$ represents a hydrogen atom or a methyl group;

(B-2) a monoalkyl (having 6 to 18 carbon atoms) or monoalkenyl (having 6 to 18 carbon atoms) glyceryl ether; and (C) a water-soluble salt.

Hereinafter, each component is described in detail. Component (A):

In the sulfate surfactant represented by the general formula (1), the average number of carbon atoms in the saturated or unsaturated hydrocarbon group represented by $R^1$ in the general formula (1) is 8 to 18, preferably 8 to 16, more preferably 10 to 14, and further preferably 12 to 14. Furthermore, in terms of the performance such as a foaming force and how fine the foam is, $R^1$ is preferably a linear alkyl group derived from fat and oils raw materials. Specific examples include an octyl group, a decyl group, a lauryl group, a myristyl group, a cetyl group, and a stearyl group and the like.

The average mole number of added PO in the general formula (1) is a number within the range of $0<m<1$. However, in terms of the foamability and stability at low temperatures, m is preferably 0.1 to 0.9, more preferably 0.2 to 0.9, more preferably 0.2 to 0.8, and more preferably 0.3 to 0.8.

Furthermore, the average mole number of added EO in the general formula (1) is a number within the range of $0<n<5$. However, in terms of the foamability and stability at low temperatures, n is preferably 0.5 to 4.0, more preferably 1.0 to 3.0, and more preferably 1.0 to 2.0.

From a comprehensive viewpoint of reactivity, foamability and stability at low temperatures at the time of manufacturing, the average mole number of added PO and EO are preferably 0.1 to 0.9 of PO and 0.5 to 4.0 of EO, respectively; more preferably 0.2 to 0.9 of PO and 1.0 to 3.0 of EO, respectively; and more preferably 0.3 to 0.8 of PO and 1.0 to 2.0 of EO, respectively.

Furthermore, M in the general formula (1) is a cation which forms a salt, including an alkali metal ion, an alkali earth metal ion, a basic amino acid, an ammonium ion, and an alkanol ammonium ion and the like. Specifically, examples of the alkali metal ion include a sodium ion, a potassium ion, and a lithium ion and the like. Examples of the alkali earth metal ion include a calcium ion and the like. Examples of the alkanol ammonium ion include a triethanol ammonium ion and the like. Among them, an ammonium ion, a sodium ion, and a potassium ion are more preferred, and the ammonium ion and the sodium ion are more preferred.

The addition order of PO and EO in the sulfate surfactant represented by the general formula (1) may be random on the condition that the average mole number of added PO and EO are respectively in the above-mentioned ranges. However, in order to obtain the advantages of the present invention, it is preferable that PO and EO are added in the order shown in the general formula (1), that is, firstly PO is added and then EO is added. Such alkyl ether sulfate can be produced by a method including the following steps (I) to (III), for example:

Step (I): allowing more than 0 moles and less than 1 mole in average of propylene oxide to be added to 1 mole of alcohol having an average number of carbon atoms of 8 to 18;

Step (II): allowing more than 0 moles and less than 5 moles in average of ethylene oxide to be added to 1 mole of the propylene oxide adduct obtained in the step (I); and Step (III): sulfating alkoxylate obtained in the step (II), and then neutralizing the resulting product.

The average number of carbon atoms in the alcohol to be used in the step (I) is 8 to 18. However, in terms of the versatility and handling property of raw materials, the average number of carbon atoms is preferably 8 to 16, more preferably 10 to 14, and more preferably 12 to 14. Furthermore, in terms of the performance such as a foaming force and the foam quality, a linear alkyl group is preferred.

The amount of propylene oxide to be used for reaction with the above-mentioned alcohol may be any amounts as long as a predetermined mole number of added PO can be obtained. Furthermore, in the step (II), the amount of ethylene oxide to be used for reaction with the propylene oxide adduct obtained in the step (I) may also be any amounts as long as a predetermined mole number of added EO can be obtained.

The steps (I) and (II) can be carried out by applying conventionally known methods. That is to say, alcohol and alkali such as potassium hydroxide as a catalyst, which is 0.5 to 1 mol % with respect to alcohol, are charged into an autoclave, heated and dehydrated, and predetermined amounts of propylene oxide and ethylene oxide may be subjected to an addition reaction at temperatures of 130 to 160° C. The addition form at this time is block addition, and the addition of propylene oxide [the step (I)] and the addition of ethylene oxide [the step (II)] are carried out in this order. An autoclave to be used is desirably equipped with a stirrer, a temperature control device and an automatic introduction device.

The method for sulfating alkoxylate in the step (III) include a method using sulfur trioxide (liquid or gas), sulfur trioxide-containing gas, fuming sulfuric acid, chlorosulfonic acid, and the like. Particularly, from the viewpoint of preventing the occurrence of wasted sulfuric acid, wasted hydrochloric acid, and the like, a method of continuously supplying gaseous or liquid sulfur trioxide together with alkoxylate is preferred.

The neutralization method of the obtained sulfated product include a batch method of neutralizing while adding and stirring the resultant sulfated product into a predetermined amount of neutralizer, and a continuous method of continuously supplying the sulfated product and a neutralizer into a tube, and neutralizing the resultant sulfated product in a stirring mixer, any of which may be employed. Examples of the neutralizer include alkali metal hydroxide, ammonia, and triethanolamine and the like. Alkali metal hydroxide is preferred, and sodium hydroxide is particularly preferred.

The content of the sulfate surfactant thus obtained represented by the general formula (1) is, in terms of the transportation cost and fluidity, 40 to 75 wt. %, preferably 40 to 70 wt. %, more preferably 45 to 65 wt. %, and further preferably more than 50 wt. % and not more than 65 wt. % in the surfactant composition of the present invention.

The component (B) is one or more of compound(s) selected from the group consisting of the following (B-1) and (B-2):

(B-1) an alkylene oxide adduct of alcohol represented by the following general formula (2):

$$R^2O-(AO)_t-R^3 \quad (2)$$

wherein $R^2$ represents a linear or branched alkyl or alkenyl group having 8 to 10 carbon atoms; AO represents an alkyleneoxy group having 2 to 4 carbon atoms; t represents an average mole number of added AO and represents a number of 0.5 to 4.0; and $R^3$ represents a hydrogen atom or a methyl group; and (B-2) a monoalkyl (having 6 to 18 carbon atoms) or monoalkenyl (having 6 to 18 carbon atoms) glyceryl ether.

In general formula (2), $R^2$ is a linear or branched alkyl or alkenyl group having 8 to 10 carbon atoms. In terms of reducing odor, the linear alkyl group is preferred. In terms of the foamability, $R^2$ is preferably a group having eight carbon atoms. In the case of a mixed alkyl, the mixed alkyl includes preferably not less than 50%, more preferably not less than 80%, and particularly preferably not less than 98% of the group having eight carbon atoms.

In the general formula (2), AO is an alkyleneoxy group having 2 to 4 carbon atoms and preferably a propyleneoxy group (hereinafter, referred to as "PO") and/or an ethyleneoxy group (hereinafter, referred to as "EO"). PO and EO may be block or random, but preferably block. In terms of the fluidity at low temperatures and the reducing odor, it is more preferable that PO and EO are arranged in a block structure in this order. In particular, the block including only PO is preferred.

In the compound represented by general formula (2), in terms of foamability, the average mole number t of added AO represents a number of 0.5 to 4.0, preferably a number of 1.0 to 4.0, and more preferably a number of 1.5 to 3.0.

$R^3$ in the general formula (2) is a hydrogen atom or a methyl group, preferably a hydrogen atom.

The monoalkyl (having 6 to 18 carbon atoms) or monoalkenyl (having 6 to 18 carbon atoms) glyceryl ether of the component (B-2) is preferably a compound represented by the following general formula (3). The number of carbon atoms is preferably 6 to 11, more preferably 6 to 10, further preferably 8 to 10, and particularly preferably 8.

(3)

wherein $R^4$ is a linear or branched alkyl or alkenyl group having 6 to 18 carbon atoms.

Examples of the alkyl group include an n-butyl group, an isobutyl group, a tert-butyl group, an n-pentyl group, an isopentyl group, an n-hexyl group, an isohexyl group, an n-heptyl group, an n-octyl group, an 2-ethyl hexyl group, a n-nonyl group, an n-decyl group, an isodecyl group, an n-lauryl group, and an n-isostearyl group and the like. In terms of the improvement of the foam quality, a branched chain is preferred, and mono-2-ethylhexyl glyceryl ether is preferred.

One or more of the component(s) (B) can be used. In the surfactant composition of the present invention, in terms of the fluidity and foamability after long-term storage at low temperatures, the content of the component (B) [the total content of (B-1) and (B-2)] is preferably 0.5 to 15 wt. %, more preferably 1 to 10 wt. %, and more preferably 2 to 8 wt. %. Note that the content of the component (B) is the total content of the B-1 and the B-2 (the same is applied to the following description).

In terms of the fluidity and foamability after long-term storage at low temperatures, the weight ratio of the component (A) to the component (B), (A)/(B), is preferably 99/1 to 75/25, more preferably 98/2 to 80/20, and more preferably 96/4 to 85/15.

As the water-soluble salt of the component (C), one or more of salt(s) selected from water-soluble inorganic salts and water-soluble organic salts are preferred. The water-soluble organic salt is preferably other than the surfactant. As the water-soluble salt, an amount to be dissolved to 100 g of water at 20° C. is preferably not less than 15 g, more preferably not less than 20 g, and more preferably not less than 35 g. Examples of such water-soluble salts include salts of organic acids (preferably, aliphatic organic acids) such as citric acid, malic acid, succinic acid, or lactic acid, having preferably 2 to 8 carbon atoms, and more preferably 3 to 6 carbon atoms, or salts of inorganic acids such as hydrochloric acid, sulfuric acid, nitric acid, carbonic acid, and phosphoric acid. Examples of the cation forming the salt include an alkali metal such as sodium or potassium, an alkali earth metal such as calcium and magnesium, ammonium, or aluminum and the like. Preferable specific examples of the water-soluble salts of the component (C) include alkali metal salts of inorganic acids such as sodium chloride or sodium sulfate; ammonium salts of inorganic acid such as ammonium chloride, ammonium sulfate, or ammonium nitrate; alkali metal salts of organic acids such as trisodium citrate; and ammonium salts of organic acids and the like. Particularly, alkali metal salts of inorganic acid or ammonium salts of inorganic acid are preferred. For the water-soluble salt of the component (C), one or more of salt(s) can be used.

In the surfactant composition of the present invention, in terms of the fluidity after long-term storage at low temperatures, the content of the component (C) is preferably 0.3 to 10 wt. %, more preferably 0.4 to 8 wt. %, more preferably 0.5 to 5 wt. %, and particularly preferably 1 to 4 wt. %.

In the surfactant composition of the present invention, in terms of improving the fluidity, the weight ratio of the component (A) to the component (C), (A)/(C), is preferably 99/1 to 85/15, more preferably 99/1 to 90/10, and further preferably 98/2 to 95/5.

In the surfactant composition of the present invention, in terms of improving the fluidity and imparting an excellent handling property, the viscosity at 5° C. after storage for a week at 5° C. is preferably not more than 90000 mPa·s, more preferably not more than 70000 mPa·s, and furthermore preferably not more than 50000 mPa·s. The lower limit is not particularly limited, but from viewpoint of the handling property, the viscosity may be not less than 1000 mPa·s.

In order to allow the composition to have such a viscosity, the component (B) with respect to the component (A) may be in the above-mentioned range and the component (C) with respect to the component (A) may be in the above-mentioned range.

The surfactant composition of the present invention can be produced by, for example, stirring and mixing the components (A), (B) and (C) at temperatures from 15 to 60° C. Furthermore, a form thereof is not particularly limited, but it is preferable that the form is liquid, paste, or cream. It is preferable that a solvent is used in production. Preferably, the solvent is water.

The surfactant composition of the present invention may be used as it is for a detergent composition, and, if necessary, it may be used as a detergent composition by mixing surfactants other than the components (A) and (B) and/or water.

The other surfactants to be used herein include an anionic surfactant, a non-ionic surfactant, an amphoteric surfactant, and a cationic surfactant.

Examples of the anionic surfactant include polyoxyethylene alkyl ether sulfate other than the component (A), an alkyl sulfate, a fatty acid salt, a phosphate ester salt, a sulfosuccinic acid surfactant, a sulfosuccinamate surfactant, polyoxyalkylene alkyl amide ether sulfate, monoglyceride sulfate, olefin sulfonate, alkane sulfonate, acylated isethionate, an acylated amino acid salt, polyoxyalkylene alkyl ether phosphate, and polyoxyalkylene alkyl ether acetate and the like.

Examples of the non-ionic surfactant include alkylpoly glucoside, sucrose fatty acid ester, polyglycerin fatty acid ester, polyoxyalkylene alkyl ether other than the component (B), fatty acid alkanolamide, alkylamine oxide, and fatty acid polyhydric alcohol ester and the like.

Examples of the amphoteric surfactant include an amidobetaine surfactant, an amide amino acid surfactant, a carbobetaine surfactant, a sulfobetaine surfactant, an amidosulfobetaine surfactant, an imidazoliniumbetaine surfactant, and a phosphobetaine surfactant and the like.

Examples of the cationic surfactant include quaternary ammonium salt represented by the following general formula:

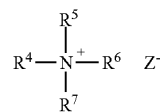

wherein at least one of $R^4$, $R^5$, $R^6$, and $R^7$ represents an alkoxy group, an alkenyloxy group or an alkanoylamino group each having 8 to 28 total carbon atoms, or an alkyl group or an alkenyl group each having 8 to 28 total carbon atoms, which may be substituted by an alkenoylamino group, others represent a benzyl group, an alkyl group having 1 to 5 carbon atoms, a hydroxyalkyl group having 1 to 5 carbon atoms or a polyoxyethylene group having a total mole number added thereof not more than 10, and Z-represents a halogen ion or an organic anion.

Examples of the detergent composition of the present invention include detergents for the skin such as a face-cleaning agent and a body shampoo; hair washing agents such as a shampoo; and a detergent for hard surface such as dish-washing detergent. Optional components can be blended, depending on their purpose of use.

The optional components, as conditioning components, include higher alcohols such as lauryl alcohol, myristyl alcohol, cetyl alcohol, or stearyl alcohol; silicone and silicone derivatives; oil solution such as lanolin, squalane, hydrocarbon, protein derivative, and polyethylene glycol fatty acid ester; a cationic polymer such as cationized cellulose, cationized guar gum, or MARCOAT 550 (manufactured by Nalco); a cationic group-containing copolymer such as Sofcare KG-301W (manufactured by Kao Corporation) and the like.

Furthermore, the other components usually used in the detergent composition can be used if necessary as long as they do not impair the advantages of the present invention. Examples of the other components include water-soluble polymers such as polysaccharides such as methyl cellulose, hydroxy ethyl cellulose, a carboxy vinyl polymer, or xanthan gum; a viscosity adjusting agent such as polyoxyalkylene sorbitan ester, polyoxyethylene glycol distearate, or ethanol; a chelating agent such as ethylene diamine tetraacetic acid (EDTA) or phosphonate; preservatives such as methylparaben and butylparaben; active components such as vitamin or precursors thereof; animal and plant extracts or derivatives thereof such as lecithin and gelatin; polymer fine powders such as nylon and polyethylene; antiphlogistic such as dipotassium glycyrrhizinate; disinfectant and antidandruff agents such as triclosan, trichlorocarban, octopirox, and zinc pyrithione; an antioxidant such as dibutylhydroxytoluene; a pearling agent; an ultraviolet absorber; a pH adjusting agent; a colorant; a perfume; or water.

In the detergent composition of the present invention, the concentration of the component (A) is preferably 5 to 25 wt. %, and more preferably 8 to 20 wt. %.

The pH (at 20° C.) of the detergent composition of the present invention is preferably from 4 to 7, and more preferably from 5 to 7.

The detergent composition of the present invention can be produced according to the usual method. Furthermore, the form thereof is not particularly limited, and any forms, for example, liquid, paste, cream, solid, and powder form, can be employed. The liquid form, paste form, and cream form are preferred. In particular, liquid form is preferred. In the case of the liquid form, it is preferable to use water as a liquid solvent.

EXAMPLE

Example 1

Hereinafter, the present invention is described in more detail with reference to the following Examples, but the present invention is not limited to these Examples. All percentages (%) and parts are by weight unless otherwise noted. Furthermore, the numeric values in Tables 4 to 6 are numeric values of pure content.

Production of Sulfate Surfactant 1

Into an autoclave equipped with a stirrer, a temperature control device, and an automatic introduction device, 3447 g of $C_{12}$ alcohol (product name: Kalcohl 2098, manufactured by Kao Corporation), 1341 g of $C_{14}$ alcohol (product name: Kalcohl 4098, manufactured by Kao Corporation) and 6.8 g of KOH were charged, followed by dehydration at 110° C. and 1.3 kPa for 30 min. After dehydration, nitrogen substitution was carried out, the resultant product was heated to 120° C., and then 575 g of propylene oxide was charged thereinto. The resultant product was subjected to addition reaction and aging at 120° C., and then heated to 145° C., and 1625 g of ethylene oxide was charged thereinto. The resultant product was subjected to addition reaction and aging at 145° C., and then cooled to 80° C., and then, unreacted EO was removed at 4.0 kPa. After the unreacted EO was removed, 7.3 g of acetic acid was added into the autoclave, stirred at 80° C. for 30 min, followed by an extraction. Thus, alkoxylate having an average mole number of added PO of 0.4 moles and an average mole number of added EO of 1.5 moles was obtained.

The alkoxylate thus obtained was sulfated with $SO_3$ gas in a falling film reactor (hereinafter, referred to as "FFR"). The obtained sulfated product was neutralized with an aqueous solution of NaOH to obtain a sulfate surfactant 1.

Similarly, sulfate surfactants 2 to 6 were obtained.

Examples 1 to 26 and Comparative Examples 1 to 11

By using the sulfate surfactants 1 to 6 (pure content: 70 wt. %) shown in Tables 1 and 2, the surfactant compositions shown in Tables 4 to 6 were prepared according to the below-mentioned method, and evaluated by the below-mentioned evaluation method. Results are shown in Tables 4 to 6.

Preparation method: the component (A) and the component (B) were mixed with the component (C) that had been dissolved in an appropriate amount of water. The mixture was adjusted by using water, so that the total was 100 parts by weight. Note here that the pH was adjusted to 6.0 (at 20° C.) with sodium hydroxide or citric acid.

Note here that alkylene glycol ethers 1 to 3 shown in Tables 4 to 6 are ones shown in Table 3.

(1) Measurement of Viscosity

The measurement conditions of a viscosity follow.

Viscometer used: B-type Viscometer (manufactured by Tokyo Keiki INC.)

Rotor No./Rotation: No. 4/6 rpm

Measurement time: 1 min.

A glass bottle containing a sample was placed in a constant temperature bath at a temperature of 30° C.: 30° C.±1 for one hour, and then measurement was carried out.

It was placed in a thermostat of at temperature of 5° C.: 5° C.±1 for one week, and taken out. Immediately after it was taken out, measurement was carried out.

(2) Fluidity

A glass bottle containing a sample was placed in a constant temperature bath at a temperature of 30° C.: 30° C.±1 for one hour, and then evaluation was carried out.

It was placed in a thermostat at a temperature of 5° C.: 5° C.±1 for one week, and taken out. Immediately after it was taken out, evaluation was carried out.

(Evaluation Method)

As the evaluation method, visual evaluation was carried out by tilting the glass bottle containing a surfactant composition 90°.

A: The surfactant composition starts to flow immediately.

B: The surfactant composition starts to flow slowly.

C: The surfactant composition does not start to flow.

(3) Foamability Test

A surfactant composition (20° C.) was prepared by diluting with ion exchanged water so that the total amount of the component (A) and component (B) was 15 wt. %. From the surfactant composition thus prepared, 1 ml of the composition was taken on the palm, it was diluted with 10 ml of tap water (35 to 40° C.), and the diluted composition was used for washing hands and arms. At this time, comparison and evaluation of the foamability was carried out according to the below-mentioned evaluation standard by ten expert panelists. The comparison and evaluation were carried out relative to a surfactant composition (20° C.) including only the sulfate surfactant 1 and adjusted to 15 wt. % as a standard product.

(Foamability)

A: An amount of foam is extremely larger as compared with the standard product.

B: An amount of foam is larger as compared with the standard product.

C: An amount of foam is the same level as that of the standard product.

D: An amount of foam is smaller as compared with the standard product.

Note here that the surfactant compositions in Tables 4 and 5 hardly form gel and were able to be easily diluted, when they were diluted to 15 wt. %.

TABLE 1

| | $R^1O$—$(PO)m(EO)nSO3M$ | $R^1$ | m | n | M |
|---|---|---|---|---|---|
| 1 | Sulfate surfactant 1 | C12/C14 (Molar ratio: 75/25) | 0.4 | 1.5 | Na |
| 2 | Sulfate surfactant 2 | C12/C14 (Molar ratio: 75/25) | 0.6 | 1.5 | Na |
| 3 | Sulfate surfactant 3 | C12 | 0.2 | 1.5 | Na |
| 4 | Sulfate surfactant 4 | C12/C14 (Molar ratio: 75/25) | 0.5 | 3.5 | NH4 |

$R^1$: C12/C14, C12 are linear alkyl groups.

TABLE 2

| | $R^1O$—$(PO)m(EO)nSO3M$ | $R^1$ | m | n | M |
|---|---|---|---|---|---|
| 5 | Sulfate surfactant 5 | C12/C14 (Molar ratio: 75/25) | 0 | 2 | Na |
| 6 | Sulfate surfactant 6 | C12/C14 (Molar ratio: 75/25) | 2 | 2 | Na |

$R^1$: C12/C14 are linear alkyl groups.

TABLE 3

| | $R^2O$—$(AO)t$—$R3$ | R2 | R3 | (AO)t |
|---|---|---|---|---|
| 1 | Alkylene glycol ether 1 | C8 | H | (PO)2.8 |
| 2 | Alkylene glycol ether 2 | C8 | H | (PO)1.5 |
| 3 | Alkylene glycol ether 3 | 2-ethylhexyl | H | (EO)2.5 |

$R^2$: C8 is a linear alkyl group.

TABLE 4

| | | | Examples | | | | | | | |
|---|---|---|---|---|---|---|---|---|---|---|
| | Component (%) | | 1 | 2 | 3 | 4 | 5 | 6 | 7 | 8 |
| (A) | Sulfate surfactant 1 | | 64 | 64 | 64 | | | | 64 | 60 |
| | Sulfate surfactant 2 | | | | | 64 | | | | |
| | Sulfate surfactant 3 | | | | | | 64 | | | |
| | Sulfate surfactant 4 | | | | | | | 64 | | |
| (A) Comparison | Sulfate surfactant 5 | | | | | | | | | |
| | Sulfate surfactant 6 | | | | | | | | | |
| (B) | Mono-2-ethylhexyl glyceryl ether | | 2.0 | 3.4 | 7.1 | 3.4 | 3.4 | 3.4 | 3.4 | 3.2 |
| | Monoisodecyl glyceryl ether | | | | | | | | | |
| | Monoisostearyl glyceryl ether | | | | | | | | | |
| | Alkylene glycol ether 1 | | | | | | | | | |
| | Alkylene glycol ether 2 | | | | | | | | | |
| | Alkylene glycol ether 3 | | | | | | | | | |
| (C) | Sodium chloride | | 4 | 4 | 4 | 4 | 4 | 4 | | 2.5 |
| | Sodium sulfate | | | | | | | | | |
| | Sodium carbonate | | | | | | | | 2 | |
| | Trisodium citrate | | | | | | | | | |
| | Ammonium chloride | | | | | | | | | |
| | Ammonium sulfate | | | | | | | | | |
| | Ammonium nitrate | | | | | | | | | |
| | Propylene glycol | | | | | | | | | |
| | Ethanol | | | | | | | | | |
| | Polyethylene glycol (Mw600) | | | | | | | | | |
| | Glycerin monocaprylate | | | | | | | | | |
| | Decyl glycoside | | | | | | | | | |
| Purified water | | | Balanced | Balanced | Balanced | Balanced | Balanced | Balanced | Balanced | Balanced |
| (A)/(B) (Weight ratio) | | | 97/3 | 95/5 | 90/10 | 95/5 | 95/5 | 95/5 | 95/5 | 95/5 |
| (A)/(C) (Weight ratio) | | | 94/6 | 94/6 | 94/6 | 94/6 | 94/6 | 94/6 | 97/3 | 96/4 |
| Physical property and | Viscosity (mPa·s, 30° C.) | | 21000 | 33000 | 38000 | 33300 | 32300 | 20800 | 24000 | 33500 |
| | Viscosity (mPa·s, 5° C.) | | 17000 | 25000 | 30000 | 27100 | 58000 | 23000 | 18000 | 33000 |
| | 30° C. Fluidity | | A | A | A | A | A | A | A | A |

TABLE 4-continued

| | | | | | | | | | |
|---|---|---|---|---|---|---|---|---|---|
| evaluation | 5° C. Fluidity | B | A | A | A | B | A | A | A |
| | Foamability (15% aqueous solution) | B | A | A | A | A | B | A | A |

| | | | Examples | | | | | |
|---|---|---|---|---|---|---|---|---|
| | Component (%) | | 9 | 10 | 11 | 12 | 13 | 14 |
| (A) | Sulfate surfactant 1 | | 55 | 60 | 60 | 45 | 50 | 50 |
| | Sulfate surfactant 2 | | | | | | | |
| | Sulfate surfactant 3 | | | | | | | |
| | Sulfate surfactant 4 | | | | | | | |
| (A) Comparison | Sulfate surfactant 5 | | | | | | | |
| | Sulfate surfactant 6 | | | | | | | |
| (B) | Mono-2-ethylhexyl glyceryl ether | | 2.9 | 3.2 | 3.2 | 2.4 | 2.7 | 2.7 |
| | Monoisodecyl glyceryl ether | | | | | | | |
| | Monoisostearyl glyceryl ether | | | | | | | |
| | Alkylene glycol ether 1 | | | | | | | |
| | Alkylene glycol ether 2 | | | | | | | |
| | Alkylene glycol ether 3 | | | | | | | |
| (C) | Sodium chloride | | | | | | 2 | 3 |
| | Sodium sulfate | | | | | | | |
| | Sodium carbonate | | | | | | | |
| | Trisodium citrate | | | | | | | |
| | Ammonium chloride | | 2 | | | 3 | | 3 |
| | Ammonium sulfate | | | 2 | | | | |
| | Ammonium nitrate | | | | | | | |
| | Propylene glycol | | | | | | | |
| | Ethanol | | | | | | | |
| | Polyethylene glycol (Mw600) | | | | | | | |
| | Glycerin monocaprylate | | | | | | | |
| | Decyl glycoside | | | | | | | |
| | Purified water | | Balanced | Balanced | Balanced | Balanced | Balanced | Balanced |
| | (A)/(B) (Weight ratio) | | 95/5 | 95/5 | 95/5 | 95/5 | 95/5 | 95/5 |
| | (A)/(C) (Weight ratio) | | 97/3 | 97/3 | 97/3 | 96/4 | 96/4 | 96/4 |
| Physical property and evaluation | Viscosity (mPa·s, 30° C.) | | 8500 | 22500 | 12500 | 6200 | 5200 | 4500 |
| | Viscosity (mPa·s, 5° C.) | | 12000 | 19000 | 17000 | 9000 | 6300 | 6000 |
| | 30° C. Fluidity | | A | A | A | A | A | A |
| | 5° C. Fluidity | | A | A | A | A | A | A |
| | Foamability (15% aqueous solution) | | A | A | A | A | A | A |

TABLE 5

| | | Examples | | | | | | |
|---|---|---|---|---|---|---|---|---|
| | Component (%) | 15 | 16 | 17 | 18 | 19 | 20 | 21 |
| (A) | Sulfate surfactant 1 | 64 | 64 | 64 | 64 | 64 | 64 | 64 |
| | Sulfate surfactant 2 | | | | | | | |
| | Sulfate surfactant 3 | | | | | | | |
| | Sulfate surfactant 4 | | | | | | | |
| (A) Comparison | Sulfate surfactant 5 | | | | | | | |
| | Sulfate surfactant 6 | | | | | | | |
| (B) | Mono-2-ethylhexyl glyceryl ether | | | | | | | |
| | Monoisodecyl glyceryl ether | 3.4 | | | | | | |
| | Monoisostearyl glyceryl ether | | 3.4 | | | | 7.1 | |
| | Alkylene glycol ether 1 | | | 3.4 | | | | 7.1 |
| | Alkylene glycol ether 2 | | | | 3.4 | | | |
| | Alkylene glycol ether 3 | | | | | 3.4 | | |
| (C) | Sodium chloride | 4 | 4 | 4 | 4 | 4 | 1.3 | 1.3 |
| | Sodium sulfate | | | | | | | |
| | Sodium carbonate | | | | | | | |
| | Trisodium citrate | | | | | | | |
| | Ammonium chloride | | | | | | | |
| | Ammonium sulfate | | | | | | | |
| | Ammonium nitrate | | | | | | | |
| | Propylene glycol | | | | | | | |
| | Ethanol | | | | | | | |
| | Polyethylene glycol | | | | | | | |

TABLE 5-continued

|  |  |  |  |  |  |  |  |  |
|---|---|---|---|---|---|---|---|---|
|  | (Mw600) |  |  |  |  |  |  |  |
|  | Glycerin monocaprylate |  |  |  |  |  |  |  |
|  | Decyl glycoside |  |  |  |  |  |  |  |
| Purified water |  | Balanced | Balanced | Balanced | Balanced | Balanced | Balanced | Balanced |
| (A)/(B) (Weight ratio) |  | 95/5 | 95/5 | 95/5 | 95/5 | 95/5 | 90/10 | 90/10 |
| (A)/(C) (Weight ratio) |  | 94/6 | 94/6 | 94/6 | 94/6 | 94/6 | 98/2 | 98/2 |
| Physical | Viscosity (mPa · s, 30° C.) | 14200 | 14000 | 17400 | 17500 | 15500 | 15500 | 15500 |
| property | Viscosity (mPa · s, 5° C.) | 20000 | 19000 | 15500 | 15050 | 16500 | 23000 | 20500 |
| and | 30° C. Fluidity | A | A | A | A | A | A | A |
| evaluation | 5° C. Fluidity | A | A | A | A | A | A | A |
|  | Foamability (15% aqueous solution) | A | B | A | A | A | A | B |

|  |  |  | Examples |  |  |  |  |
|---|---|---|---|---|---|---|---|
|  | Component (%) |  | 22 | 23 | 24 | 25 | 26 |
| (A) | Sulfate surfactant 1 |  | 50 |  | 60 | 60 |  |
|  | Sulfate surfactant 2 |  |  | 64 |  |  | 64 |
|  | Sulfate surfactant 3 |  |  |  |  |  |  |
|  | Sulfate surfactant 4 |  |  |  |  |  |  |
| (A) | Sulfate surfactant 5 |  |  |  |  |  |  |
| Comparison | Sulfate surfactant 6 |  |  |  |  |  |  |
| (B) | Mono-2-ethylhexyl glyceryl ether |  |  |  | 3.2 | 3.2 | 3.2 |
|  | Monoisodecyl glyceryl ether |  |  |  |  |  |  |
|  | Monoisostearyl glyceryl ether |  |  |  |  |  |  |
|  | Alkylene glycol ether 1 |  | 2.7 |  |  |  |  |
|  | Alkylene glycol ether 2 |  |  | 3.4 |  |  |  |
|  | Alkylene glycol ether 3 |  |  |  |  |  |  |
| (C) | Sodium chloride |  |  |  | 1.3 |  | 1.2 |
|  | Sodium sulfate |  |  |  |  |  |  |
|  | Sodium carbonate |  |  |  |  |  |  |
|  | Trisodium citrate |  |  |  |  | 1.9 |  |
|  | Ammonium chloride |  | 3 |  |  |  |  |
|  | Ammonium sulfate |  |  |  |  |  |  |
|  | Ammonium nitrate |  |  |  |  | 1.9 |  |
|  | Propylene glycol |  |  |  |  |  |  |
|  | Ethanol |  |  |  |  |  |  |
|  | Polyethylene glycol (Mw600) |  |  |  |  |  |  |
|  | Glycerin monocaprylate |  |  |  |  |  |  |
|  | Decyl glycoside |  |  |  |  |  |  |
| Purified water |  |  | Balanced | Balanced | Balanced | Balanced | Balanced |
| (A)/(B) (Weight ratio) |  |  | 95/5 | 95/5 | 95/5 | 95/5 | 95/5 |
| (A)/(C) (Weight ratio) |  |  | 94/6 | 98/2 | 97/3 | 97/3 | 98/2 |
| Physical | Viscosity (mPa · s, 30° C.) |  | 6870 | 16500 | 11000 | 12300 | 21500 |
| property | Viscosity (mPa · s, 5° C.) |  | 9480 | 20000 | 17000 | 22500 | 29000 |
| and | 30° C. Fluidity |  | A | A | A | A | A |
| evaluation | 5° C. Fluidity |  | A | B | A | A | B |
|  | Foamability (15% aqueous solution) |  | A | A | A | A | B |

TABLE 6

|  |  | Comparative examples |  |  |  |  |  |  |
|---|---|---|---|---|---|---|---|---|
|  | Component (%) | 1 | 2 | 3 | 4 | 5 | 6 | 7 |
| (A) | Sulfate surfactant 1 | 64 | 60 | 64 | 64 | 64 | 64 | 64 |
|  | Sulfate surfactant 2 |  |  |  |  |  |  |  |
|  | Sulfate surfactant 3 |  |  |  |  |  |  |  |
|  | Sulfate surfactant 4 |  |  |  |  |  |  |  |
| (A) | Sulfate surfactant 5 |  |  |  |  |  |  |  |
| Comparison | Sulfate surfactant 6 |  |  |  |  |  |  |  |
| (B) | Mono-2-ethylhexyl glyceryl ether |  |  |  |  | 3.4 |  |  |
|  | Monoisodecyl glyceryl ether |  |  |  |  |  |  |  |
|  | Monoisostearyl glyceryl ether |  |  |  |  |  |  |  |
|  | Alkylene glycol ether 1 |  |  |  |  |  |  |  |
|  | Alkylene glycol ether 2 |  |  |  |  |  |  |  |
|  | Alkylene glycol ether 3 |  |  |  |  |  |  |  |

TABLE 6-continued

|  |  |  |  |  |  |  |  |  |
|---|---|---|---|---|---|---|---|---|
| (C) | Sodium chloride |  |  | 4 | 2 |  |  |  |
|  | Sodium sulfate |  |  |  |  |  |  |  |
|  | Sodium carbonate |  |  |  |  |  |  |  |
|  | Trisodium citrate |  |  |  |  |  |  |  |
|  | Ammonium chloride |  |  |  |  |  |  |  |
|  | Ammonium sulfate |  |  |  |  |  |  |  |
|  | Ammonium nitrate |  |  |  |  |  |  |  |
|  | Propylene glycol |  |  |  |  |  | 3.4 |  |
|  | Ethanol |  |  |  |  |  |  | 3.4 |
|  | Polyethylene glycol (Mw600) |  |  |  |  |  |  |  |
|  | Glycerin monocaprylate |  |  |  |  |  |  |  |
|  | Decyl glycoside |  |  |  |  |  |  |  |
| Purified water |  | Balanced | Balanced | Balanced | Balanced | Balanced | Balanced | Balanced |
| (A)/(B) (Weight ratio) |  | 100/0 | 100/0 | 100/0 | 100/0 | 95/5 | 100/0 | 100/0 |
| (A)/(C) (Weight ratio) |  | 100/0 | 100/0 | 94/6 | 96/4 | 100/0 | 100/0 | 100/0 |
| Physical property and evaluation | Viscosity (mPa·s, 30° C.) | 24600 | Not less than 100000 | 11900 | 7200 | 94500 | 21000 | 26500 |
|  | Viscosity (mPa·s, 5° C.) | Not less than 100000 | Not less than 100000 | Not less than 100000 | Not less than 100000 | 94000 | Not less than 100000 | Not less than 100000 |
|  | 30° C. Fluidity | B | C | A | A | C | B | B |
|  | 5° C. Fluidity | C | C | C | C | C | C | C |
|  | Foamability (15% aqueous solution) | C | C | C | C | A | D | D |

|  |  |  | Comparative examples | | | | |
|---|---|---|---|---|---|---|---|
|  |  | Component (%) | 8 | 9 | 10 | 11 | 12 |
| (A) |  | Sulfate surfactant 1 | 64 | 64 | 64 |  |  |
|  |  | Sulfate surfactant 2 |  |  |  |  |  |
|  |  | Sulfate surfactant 3 |  |  |  |  |  |
|  |  | Sulfate surfactant 4 |  |  |  |  |  |
| (A) |  | Sulfate surfactant 5 |  |  |  | 64 |  |
| Comparison |  | Sulfate surfactant 6 |  |  |  |  | 64 |
| (B) |  | Mono-2-ethylhexyl glyceryl ether |  |  |  | 3.4 | 3.4 |
|  |  | Monoisodecyl glyceryl ether |  |  |  |  |  |
|  |  | Monoisostearyl glyceryl ether |  |  |  |  |  |
|  |  | Alkylene glycol ether 1 |  |  |  |  |  |
|  |  | Alkylene glycol ether 2 |  |  |  |  |  |
|  |  | Alkylene glycol ether 3 |  |  |  |  |  |
| (C) |  | Sodium chloride |  |  | 4 | 4 | 4 |
|  |  | Sodium sulfate |  |  |  |  |  |
|  |  | Sodium carbonate |  |  |  |  |  |
|  |  | Trisodium citrate |  |  |  |  |  |
|  |  | Ammonium chloride |  |  |  |  |  |
|  |  | Ammonium sulfate |  |  |  |  |  |
|  |  | Ammonium nitrate |  |  |  |  |  |
|  |  | Propylene glycol |  |  |  |  |  |
|  |  | Ethanol |  |  |  |  |  |
|  |  | Polyethylene glycol (Mw600) | 3.4 |  |  |  |  |
|  |  | Glycerin monocaprylate |  | 3.4 |  |  |  |
|  |  | Decyl glycoside |  |  | 3.4 |  |  |
| Purified water |  |  | Balanced | Balanced | Balanced | Balanced | Balanced |
| (A)/(B) (Weight ratio) |  |  | 100/0 | 100/0 | 100/0 | 95/5 | 95/5 |
| (A)/(C) (Weight ratio) |  |  | 100/0 | 100/0 | 94/6 | 94/6 | 94/6 |
| Physical property and evaluation | Viscosity (mPa·s, 30° C.) |  | 25600 | 14500 | 14000 | 13500 | 13500 |
|  | Viscosity (mPa·s, 5° C.) |  | Not less than 100000 | Not less than 100000 | Not less than 100000 | Not less than 100000 | 28000 |
|  | 30° C. Fluidity |  | B | B | A | A | A |
|  | 5° C. Fluidity |  | C | C | C | C | A |
|  | Foamability (15% aqueous solution) |  | D | B | B | B | D |

It is shown that the product of the present invention has a low viscosity and excellent fluidity at a low temperature (5° C.) even after storage for a week, and therefore it has an excellent handling property in winter season and further has excellent foamability.

It is shown that the sulfate surfactant in which only EO is added, shown in Comparative Example 11 has a high viscosity at a low temperature (5° C.), is inferior in fluidity and somewhat inferior in foamability.

It is shown that the sulfate surfactant having a large average mole number of added PO, shown in Comparative Example 12 is inferior in foamability.

Example 27

A body shampoo having the following compositions was produced.

| (Components) | (wt. %) |
|---|---|
| surfactant composition of Example 5 | 5.0 |
| sodium laurate | 6.0 |
| sodium myristate | 3.0 |
| sodium palmitate | 1.0 |
| 2-ethyl hexyl glyceryl ether | 1.0 |
| glycerin | 3.0 |
| methylparaben | appropriate amount |
| perfume | appropriate amount |
| purified water | balanced |
| Total | 100.0 |

In this body shampoo, the surfactant composition of Example 5 does not undergo viscosity increase when diluted, and can be easily blended. This body shampoo has good foamability, and has an excellent usability.

Example 28

A shampoo having the following compositions was produced.

| (Components) | (wt. %) |
|---|---|
| surfactant composition of Example 2 | 15.0 |
| amidopropyl betaine* | 2.0 |
| myristyl alcohol | 1.0 |
| cationized guar gum** | 0.5 |
| ethanol | 3.0 |
| perfume | appropriate amount |
| purified water | balanced |
| Total | 100.0 |

*AMPHITOL 20AB (manufactured by Kao Corporation)
**JAGUAR C-13S (manufactured by Rhodia)

In this shampoo, the surfactant composition of Example 2 does not undergo viscosity increase when diluted, and can be easily blended. This shampoo has good foamability, and has an excellent usability.

Example 29

A shampoo having the following compositions was produced.

| (Components) | (wt. %) |
|---|---|
| surfactant composition of Example 17 | 16.0 |
| coconut oil fatty acid N-methyl ethanol amide* | 1.0 |
| myristyl alcohol | 1.0 |
| cationized guar gum** | 0.5 |
| ethanol | 3.0 |
| perfume | appropriate amount |
| purified water | balanced |
| Total | 100.0 |

*AMINON C-11S (manufactured by Kao Corporation)
**JAGUAR C-13S (manufactured by Rhodia)

In this shampoo, the surfactant composition of Example 17 does not undergo viscosity increase when diluted, and can be easily blended. This shampoo has good foamability, and has an excellent usability.

Example 30

A shampoo having the following compositions was produced.

| (Components) | (wt. %) |
|---|---|
| surfactant composition of Example 22 | 17.0 |
| silicone emulsion* | 2.0 |
| cationized cellulose** | 0.5 |
| lauryl hydroxysulfobetaine*** | 5.0 |
| glycerin | 3.0 |
| perfume, methylparaben | appropriate amount |
| purified water | balanced |
| Total | 100.0 |

*BY22-050A [manufactured by Dow Corning Toray]
**POIZ C-150L [manufactured by Kao Corporation]
***AMPHITOL 20HD [manufactured by Kao Corporation]

In this shampoo, the surfactant composition of Example 22 does not undergo viscosity increase when diluted, and can be easily blended. This shampoo has good foamability, and has an excellent usability.

Example 31

A dish-washing detergent having the following compositions was produced.

| (Components) | (wt. %) |
|---|---|
| surfactant composition of Example 17 | 27.0 |
| amine oxide* | 9.0 |
| lauryl hydroxysulfobetaine** | 10.0 |
| magnesium chloride hexahydrate | 3.0 |
| sodium p-toluenesulfonate | 10.0 |
| ethanol | 2.5 |
| propylene glycol | 5.0 |
| pH adjusting agent*** | appropriate amount |
| perfume, methylparaben | appropriate amount |
| purified water | balanced |
| Total | 100.0 |

*AMPHITOL 20N [manufactured by Kao Corporation]
**AMPHITOL 20HD [manufactured by Kao Corporation]
***citric acid or sodium hydroxide In this dish-washing detergent, the surfactant composition of Example 17 does not undergo viscosity increase when diluted, and can be easily blended. This dish-washing detergent has good foamability, and has an excellent usability.

Example 32

A conditioning shampoo having the following compositions was produced.

| (Components) | (wt. %) |
|---|---|
| surfactant composition of Example 13 | 24.0 |
| cocoyl monoethanol amide | 0.8 |
| myristyl alcohol | 1.0 |
| cationic group-containing copolymer* | 5.0 |
| cationized cellulose** | 0.4 |
| silicone emulsion*** | 2.5 |
| perfume | appropriate amount |
| purified water | balanced |
| Total | 100.0 |

*Sofcare KG301W (manufactured by Kao Corporation)
**POIZ C-150L (manufactured by Kao Corporation)
***BY22-060 [manufactured by Dow Corning Toray]

In this shampoo, the surfactant composition of Example 13 does not undergo viscosity increase when diluted, and can be easily blended. This shampoo has good foamability, and has an excellent usability.

The invention claimed is:

1. A surfactant composition comprising the following components (A), (B) and (C), wherein a content of the component (A) is more than 50 wt. % and not more than 65 wt. %:
    (A) a sulfate surfactant represented by the following general formula (1):

$$R^1O\text{---}(PO)_m(EO)_nSO_3M \quad (1)$$

wherein $R^1$ represents a saturated or unsaturated hydrocarbon group having 8 to 18 carbon atoms; PO represents a propyleneoxy group; EO represents an ethyleneoxy group; m and n represent an average mole number of added PO and EO, respectively, are the same as or different from each other, and independently represent a number within the ranges of $0.1<m<0.9$ and $0.5<n<4.0$; and M represents a cation;
    (B) one or more of compound(s) selected from the group consisting of the following (B-1) and (B-2):
        (B-1) an alkylene oxide adduct of alcohol represented by the following general formula (2):

$$R^2O\text{---}(AO)_t\text{---}R^3 \quad (2)$$

wherein $R^2$ represents a linear or branched alkyl or alkenyl group having 8 to 10 carbon atoms; AO represents an alkyleneoxy group having 2 to 4 carbon atoms; t represents an average mole number of added AO and represents a number of 0.5 to 4.0; and $R^3$ represents a hydrogen atom or a methyl group;
        (B-2) a monoalkyl having 6 to 18 carbon atoms or monoalkenyl having 6 to 18 carbon atoms glyceryl ether; and
    (C) a water-soluble salt selected from the group consisting of sodium chloride, sodium sulfate, sodium carbonate, trisodium citrate, ammonium chloride, ammonium sulfate, and ammonium nitrate; wherein a weight ratio of the components (A) to the components (B), (A)/(B), is 99/1 to 75/25, and a weight ratio of the component (A) to the component (C), (A)/(C), is 99/1 to 85/15.

2. The surfactant composition according to claim 1, wherein a viscosity at 5° C. after storage for a week at 5° C. is not more than 90000 mPa·s.

3. The surfactant composition according to claim 1, wherein the content of (C) the water-soluble salt is 0.3 to 10 wt. %.

4. A detergent composition obtained by mixing the surfactant composition according to claim 1, with a surfactant other than the component (A) and the component (B) and/or water.

5. A detergent composition obtained by mixing the surfactant composition according to claim 2, with a surfactant other than the component (A) and the component (B) and/or water.

6. A detergent composition obtained by mixing the surfactant composition according to claim 3, with a surfactant other than the component (A) and the component (B) and/or water.

* * * * *